(12) United States Patent
Cho

(10) Patent No.: US 9,713,514 B2
(45) Date of Patent: Jul. 25, 2017

(54) IMPLANT ABUTMENT

(71) Applicant: Sang Choon Cho, New York, NY (US)

(72) Inventor: Sang Choon Cho, New York, NY (US)

(73) Assignee: EBI CO., LTD. (KR)

( * ) Notice: Subject to any disclaimer, the term of this patent is extended or adjusted under 35 U.S.C. 154(b) by 149 days.

(21) Appl. No.: 14/570,568

(22) Filed: Dec. 15, 2014

(65) Prior Publication Data

US 2015/0099242 A1 Apr. 9, 2015

Related U.S. Application Data

(63) Continuation of application No. PCT/KR2013/003488, filed on Apr. 24, 2013.

(30) Foreign Application Priority Data

Jun. 15, 2012 (KR) ........................ 10-2012-0064589

(51) Int. Cl.
*A61C 1/12* (2006.01)
*A61C 8/00* (2006.01)
*A61C 13/273* (2006.01)

(52) U.S. Cl.
CPC .......... *A61C 8/0068* (2013.01); *A61C 8/0001* (2013.01); *A61C 8/0048* (2013.01); *A61C 8/0063* (2013.01); *A61C 13/273* (2013.01)

(58) Field of Classification Search
CPC ....... A61C 1/12; A61C 8/0051; A61C 8/0068; A61C 8/0074
See application file for complete search history.

(56) References Cited

U.S. PATENT DOCUMENTS 5,145,369 A * 9/1992 Lustig .................... A61C 17/00
433/118
5,626,474 A * 5/1997 Kukla .................. A61C 8/0089
433/141

(Continued)

FOREIGN PATENT DOCUMENTS

JP 2002153493 A 5/2002
KR 20060012036 A 2/2006

OTHER PUBLICATIONS

International Search Report & Written Opinion of the International Searching Authority Application No. PCT/KR2013/003488 Jul. 17, 2013; Mailing Date: Jul. 18, 2013 6 pages.

*Primary Examiner* — Bruce E Snow
(74) *Attorney, Agent, or Firm* — St Longe Steward Johnston and Reens LLC

(57) ABSTRACT

Provided are related to implant abutments. The implant abutment that is coupled to a fixture that becomes an artificial tooth root by being implanted to an alveolar bone, the implant abutment includes: a main body; a first rotating member that is coupled to the main body to be able to rotate with respect to a first rotational axis, includes a first gear portion on an end portion thereof, and includes a male screw portion that is formed on the other end portion thereof to be screw coupled to the fixture; and a second rotating member that is coupled to the main body to be able to rotate with respect to a second rotational axis which crosses the first rotational axis, and includes a second gear portion that is formed on the other end portion thereof to form a bevel gear structure by being coupled to the first gear portion. The implant abutment that can readily ensure a space for coupling work of a fixture in an oral cavity of a patient since a coupling tool, such as a hex screwdriver can be readily placed in a horizontal direction which intersects the direction of implanting the fixture.

8 Claims, 8 Drawing Sheets

(56) References Cited

U.S. PATENT DOCUMENTS

| | | | |
|---|---|---|---|
| 5,660,545 A | 8/1997 | Bailey et al. | |
| 5,989,028 A | 11/1999 | Niznick | |
| 6,663,388 B1 | 12/2003 | Schar et al. | |
| 2008/0311544 A1* | 12/2008 | Lee | A61C 8/005 433/173 |

* cited by examiner

IMPLANT ABUTMENT

FIELD OF THE INVENTION

The inventive concept relates to an implant abutment, and more particularly, to an implant abutment that can readily ensure a space for coupling work of a fixture in an oral cavity of a patient since a coupling tool, such as a hex screwdriver can be readily placed in a horizontal direction which intersects the direction of implanting the fixture.

BACKGROUND OF THE INVENTION

A dental implant is referred to as an artificial tooth or a third teeth, and is a therapy method for restoring the function of natural teeth by implanting a biocompatible implant main body in a jawbone where there is a loss of teeth or a tooth is pulled out.

A dental implant generally includes a fixture that is an artificial tooth by being implanted in an alveolar bone; an implant abutment which is an abutment to be screw coupled to an upper part of the fixture; and a crown that is a tooth shape prosthetic appliance to be coupled to an upper part of the abutment.

A conventional implant abutment is a member having a simple screw shape and is screw-coupled to the fixture by a driver that is disposed in a vertical direction parallel to the implant abutment in a state that the implant abutment is disposed in a vertical direction parallel to a implanting direction of the fixture above the fixture.

However, in the case of the conventional implant abutment, the driver which is a coupling tool must be located in a vertical direction parallel to the fixture and the implant abutment, and thus, when an implanting location for coupling work is not favorable, it is difficult to ensure a working space for coupling the implant abutment in a mouth of a patient.

Also, in the case of the conventional implant abutment, in order to ensure a working space for coupling the implant abutment, a patient must open his mouth as large as possible. Accordingly, the patient may feel physical inconvenience, and furthermore, the opened mouth must be kept for long hours during the coupling operation.

SUMMARY OF THE INVENTION

Technical Problem

The inventive concept provides an implant abutment having a structure in which a working space for coupling a fixture to an abutment is easily ensured in an oral cavity of a patient's mouth since a coupling tool, such as a hex screwdriver is placed in a horizontal direction which intersects the direction of implanting the fixture.

Technical Solution

According to an aspect of the inventive concept, there is provided an implant abutment that is coupled to a fixture that becomes an artificial tooth root by being implanted to an alveolar bone, the implant abutment includes: a main body portion; a first rotating member that is coupled to the portion main body to be able to rotate with respect to a first rotational axis, includes a first gear portion on an end portion thereof, and includes a male screw portion that is screw-coupled to the fixture on the other end portion thereof; and a second rotating member that is coupled to the main body to be able to rotate with respect to a second rotational axis which crosses the first rotational axis, and includes a second gear portion that is formed on the other end portion thereof to form a bevel gear structure by being coupled to the first gear portion.

The implant abutment may further include a separation-prevention means that prevents the first gear portion of the first rotating member from being disengaged from the second gear portion of the second rotating member.

The separation-prevention means may include: a separation-prevention protrusion formed to protrude on an end portion of the first rotating member; and a separation-prevention groove that is formed on an end portion of the second rotating member and accommodates the separation-prevention protrusion in a state that the first rotating member and the second rotating member rotate.

The separation-prevention protrusion may have a cylindrical shape with the first rotational axis as a center and upwardly protrudes along the first rotational axis, and the separation-prevention groove may be concavely sunk along a circumferential direction of the second rotational axis.

The separation-prevention means may include a stopper member that is coupled to the main body and restricts the position movement of the separation-prevention groove so that the separation-prevention protrusion is fixedly positioned without being separated from the separation-prevention groove.

The stopper member may include: a lid that is coupled to the main body; a protrusion portion that protrudes from a lower surface of the lid; and an accommodation groove that is formed on an end portion of the protrusion portion and restricts the position of the second rotating member by accommodating an end portion of the second rotating member.

The main body may include: an internal space that accommodates an end portion of the first rotating member and an end portion of the second rotating member; and an upper hole that is formed on an upper end portion of the main body and is formed to insert the first rotating member into the internal space, wherein the lid is mounted in the upper hole.

An engaging portion may be formed on an outer circumferential surface of the lid, and an engaged portion that is engaged with the engaging portion is formed on an inner circumferential surface of the upper hole.

The implant abutment may further include a coupling member, an end portion thereof is coupled to the other end portion of the first rotating member and a male screw portion that is screw-coupled to the fixture is formed on the other end portion thereof.

A coupling protrusion having a protrusion shape may be formed on the other end portion of the first rotating member, a coupling groove that is coupled to the coupling protrusion to be unable to have a relative rotation with respect to the first rotating member may be formed on an end portion of the coupling member, wherein the coupling member may be able to have a relative movement with respect to the first rotating member in a direction of the first rotational axis in a state when the coupling groove is coupled to the coupling protrusion.

The main body may include: an internal space that accommodates the first rotating member and the second rotating member; an upper hole that is formed on an upper end portion of the main body so that the first rotating member is inserted into the internal space; a lower hole that is formed on a lower end portion of the main body so that the male screw portion protrudes to the outside; and a side hole that is formed on a side of the main body so that the second rotating member is inserted into the internal space.

The main body may include a protrusion portion that protrudes from an outer circumferential surface of the main body so that the main body is readily coupled to an impression material.

Advantageous Effects

According to the inventive concept, the implant abutment according to the current embodiment includes a first rotating member that is coupled to the main body to be able to rotate with respect to a first rotational axis and includes a first gear portion on an end portion thereof and a male screw portion on the other end portion thereof to be screw coupled to the fixture, and a second rotating member that is coupled to the main body to be able to rotate with respect to a second rotational axis which crosses the first rotational axis, and includes a second gear portion. Accordingly, a coupling tool, such as a hex screwdriver can be placed in a horizontal direction which intersects the direction of implanting the fixture, thereby readily ensuring a space for coupling to the fixture in a patient's mouth.

DETAILED DESCRIPTION OF THE INVENTION

Best Mode

The present invention will now be described more fully with reference to the accompanying drawings in which exemplary embodiments of the invention are shown.

Figure 1:
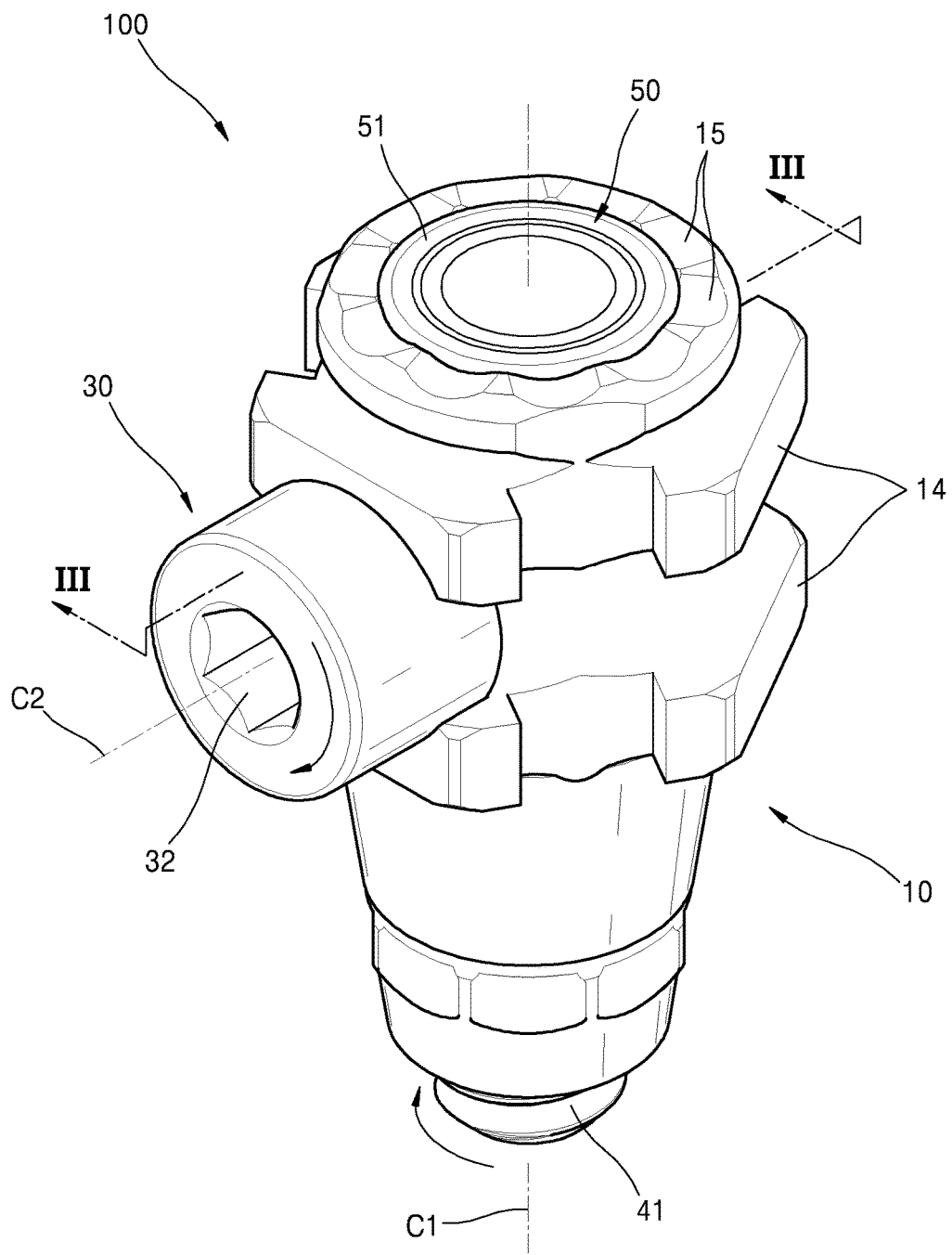
FIG. 1 is a perspective view of a coupled implant abutment according to an embodiment of the present invention.
Figure 2:
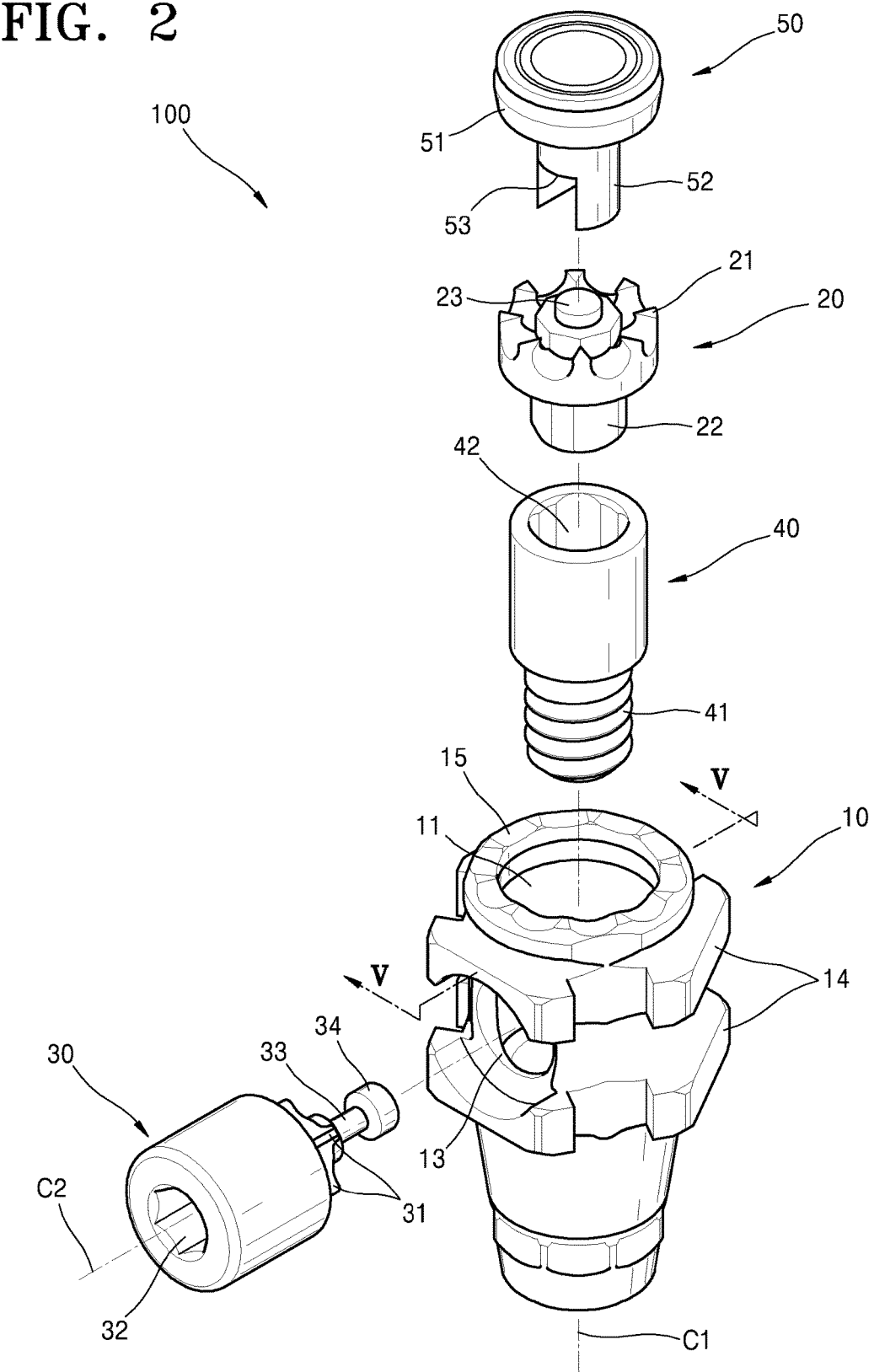
FIG. 2 is an exploded perspective view of the implant abutment of FIG. 1.
Figure 3:
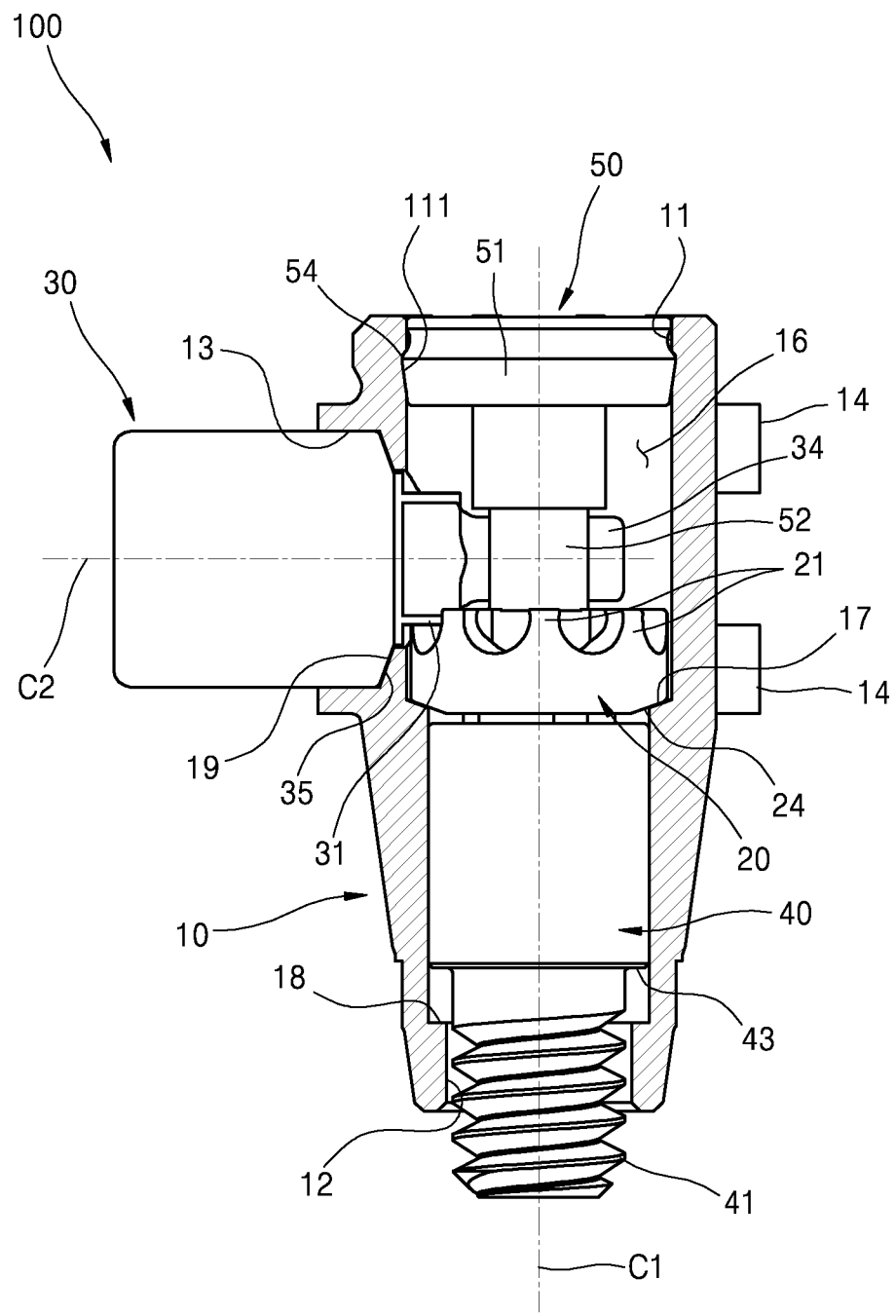
FIG. 3 is a cross-sectional view taken along line III-III of FIG. 1.

FIG. 1 is a perspective view of a coupled implant abutment 100 according to an embodiment of the present invention. FIG. 2 is an exploded perspective view of the implant abutment 100 of FIG. 1. FIG. 3 is a cross-sectional view taken along line III-III of FIG. 1.

Referring to FIGS. 1 through 3, the implant abutment 100 according to an embodiment of the inventive concept includes, a main body 10, a first rotating member 20, a second rotating member 30, a coupling member 40, a stopper member 50, and a derail prevention means as an abutment that is coupled to a fixture 1 that becomes an artificial dental root by being implanted in an alveolar bone B.

The main body 10 is a cylindrical shape metal housing having an internal space 16. An upper hole 11 and a lower hole 12 are respectively formed on an upper part and a lower part thereof, and a circular side hole 13 is formed on a side thereof.

The internal space 16 is formed to accommodate the first rotating member 20, the second rotating member 30, and the coupling member 40.

The upper hole 11 is a hole connected to the internal space 16 and has a shape and size so that the first rotating member 20 and the coupling member 40 can be inserted from the outside into the internal space 16.

An engaged portion 111 formed along a circumferential direction is provided on an inner circumferential surface of the upper hole 11.

A corrugate portion 15 that is dimply formed along a circumferential direction to be readily coupled to various resins is formed on an outer circumferential surface of the upper hole 11.

The lower hole 12 is connected to the internal space 16 and is formed to a size and shape so that a male screw portion 41 that is formed on a lower end of the coupling member 40 protrudes downwards.

In the current embodiment, the upper hole 11 and the lower hole 12 has a first rotational axis C1 extending in a vertical direction as a center of the circle.

The side hole 13 is connected to the internal space 16 and is formed to a size and shape so that the second rotating member 30 can be inserted from the outside into the internal space 16.

The side hole 13 has a second rotational axis C2 that is substantially vertically crossing the first rotational axis C1 as a center of the circle.

A projection portion 14 that protrudes in a radius direction to readily couple the main body 10 to an impression material is formed on an outer circumferential surface of an upper end portion of the main body 10.

A first stopper 17 is formed on an middle part of the internal space 16 along a circumferential direction thereof, and a second stopper 18 is formed on an inner side of the lower hole 12 along a circumferential direction thereof.

Figure 5:
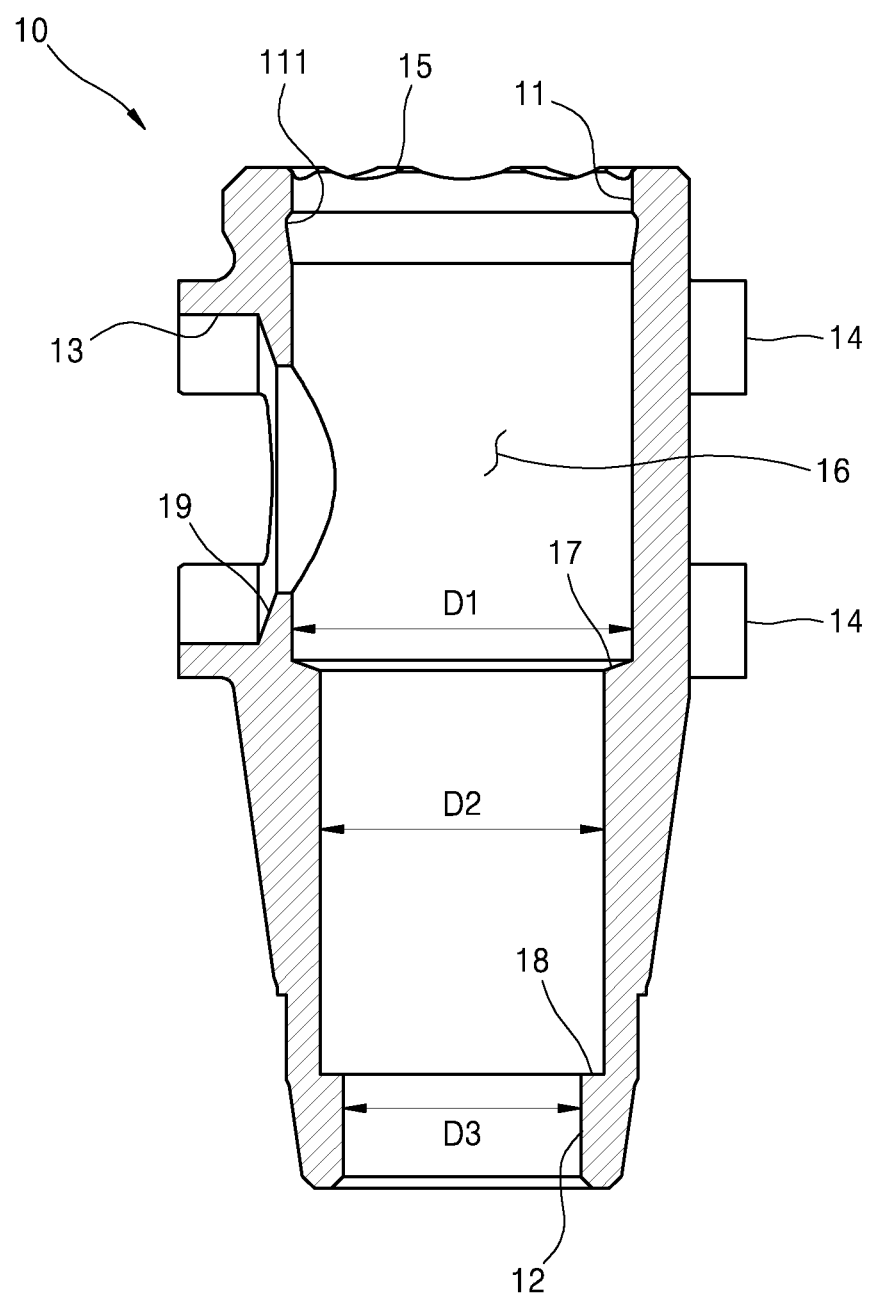
FIG. 5 is a cross-sectional view taken along line V-V of a main body of FIG. 2.
Figure 6:
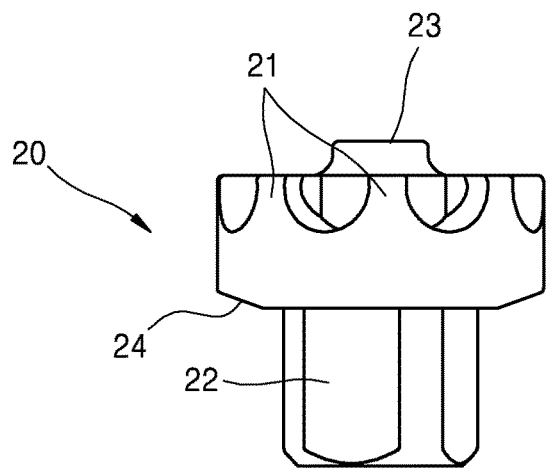
FIG. 6 is a front view of a first rotating member of the implant abutment of FIG. 2.
Figure 7:
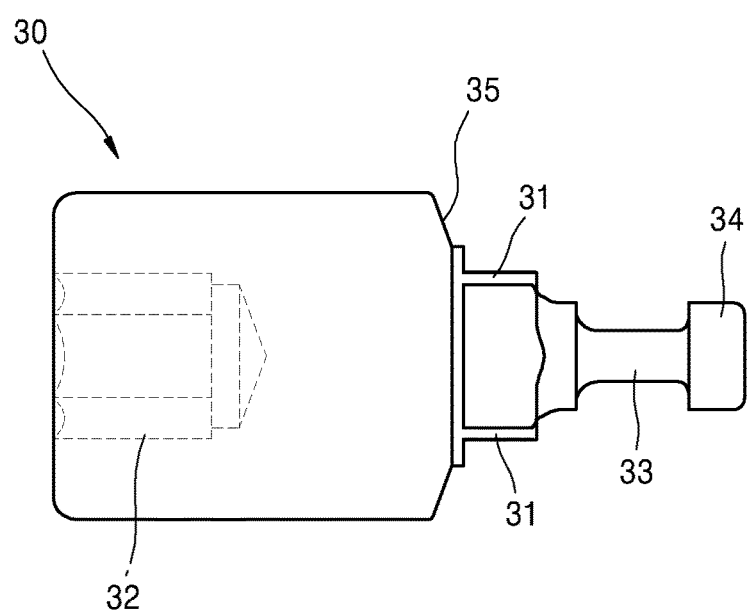
FIG. 7 is a front view of a second rotating member of the implant abutment of FIG. 2.
Figure 8:
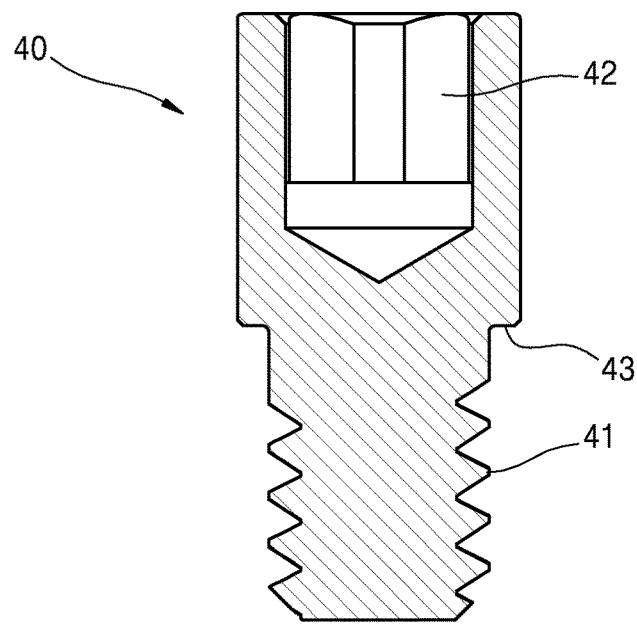
FIG. 8 is a cross-sectional view of a coupling member of the implant abutment of FIG. 2.
Figure 9:
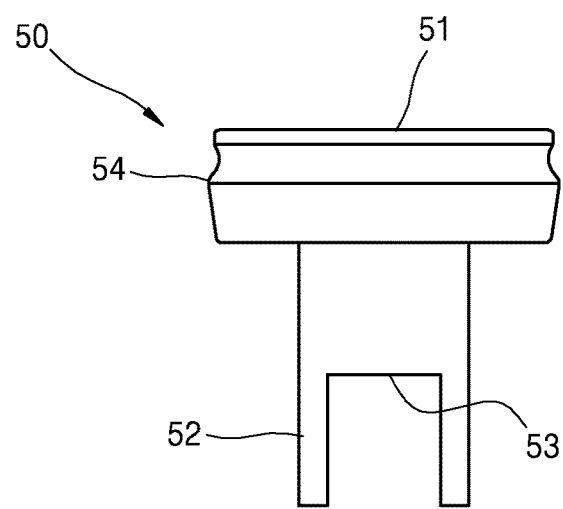
FIG. 9 is a front view of a stopper member of the implant abutment of FIG. 2.

In the current embodiment, as depicted in FIG. 5, the first and second stoppers 17 and 18 have different diameters, that is, inner diameters D1, D2, and D3 of the internal space 16 are gradually reduced from an upper side to a lower side.

A third stopper 19 is formed on an inner side of the side hole 13.

The first rotating member 20 is a cylindrical shape metal member, is inserted into the internal space 16 through the upper hole 11, and is mounted in the internal space 16 to be rotated with respect to the first rotational axis C1.

A first gear portion 21 having gear teeth that are arranged in a circular shape with the first rotational axis C1 as a center is formed on an upper end of the first rotating member 20. In the current embodiment, the gear teeth of the first gear portion 21 protrude upwards.

A separation-prevention protrusion 23 is formed to protrude upwards on a center upper end of the first rotating member 20.

The separation-prevention protrusion 23 has a cylindrical shape with the first rotational axis C1 as a center, and protrudes upwards along the first rotational axis C1.

A coupling protrusion 22 is formed to protrude downwards on a lower end of the first rotating member 20. In the current embodiment, the coupling protrusion 22 has an octagonal cross-section.

A first stopper surface 24 is formed along a circumferential direction of the first rotational axis C1 between the first gear portion 21 and the coupling protrusion 22. The first stopper surface 24 faces downwards by protruding in a radius direction of the first rotational axis C1.

The second rotating member 30 is a cylindrical shape metal member with the second rotational axis C2 as a center and an end portion of the second rotating member 30 is inserted into the side hole 13 of the main body 10. The second rotating member 30 is coupled to the main body 10 to be rotated with respect to the second rotational axis C2.

A second gear portion 31 having gear teeth that are arranged in a circular shape with the second rotational axis C2 as a center is formed on an end portion of the second rotating member 30.

The second gear portion 31 is coupled to the first gear portion 21 to form a bevel gear structure.

A third stopper surface 35 that protrudes in a radius direction of the second rotational axis C2 and faces the main body 10 is formed along a circumferential direction of the second rotational axis C2 on a left side of the second gear portion 31.

A separation-prevention groove 33 that is concavely sunk along a circumferential direction of the second rotational axis C2 is formed on a right side of the second gear portion 31.

The separation-prevention groove 33 has a size and shape that can accommodate the separation-prevention protrusion 23 of the first rotating member 20 while the first rotating member 20 and the second rotating member 30 rotate, and has a symmetrical structure with respect to the second rotational axis C2.

A circular shape head portion 34 that protrudes in a radius direction of the second rotational axis C2 is formed on a right side of the separation-prevention groove 33.

A tool hole 32 having a inwardly concaved sunk shape is formed on the other end portion of the second rotating member 30 so that a tool, such as a small wrench or a hex screw driver can be inserted. In the current embodiment, the tool hole 32 has a hexagonal cross-section.

The coupling member 40 is a cylindrical shape metal member, is inserted into the internal space 16 through the upper hole 11 of the main body 10, and is mounted on a lower end portion of the internal space 16 to be able to rotate with respect to the first rotational axis C1.

A coupling groove 42 which is a groove having an octagonal cross-section is formed on an upper end of the coupling member 40 so as to be coupled but not to be relatively rotated with respect to the coupling protrusion 22 of the first rotating member 20 with respect to the first rotational axis C1.

Figure 10:
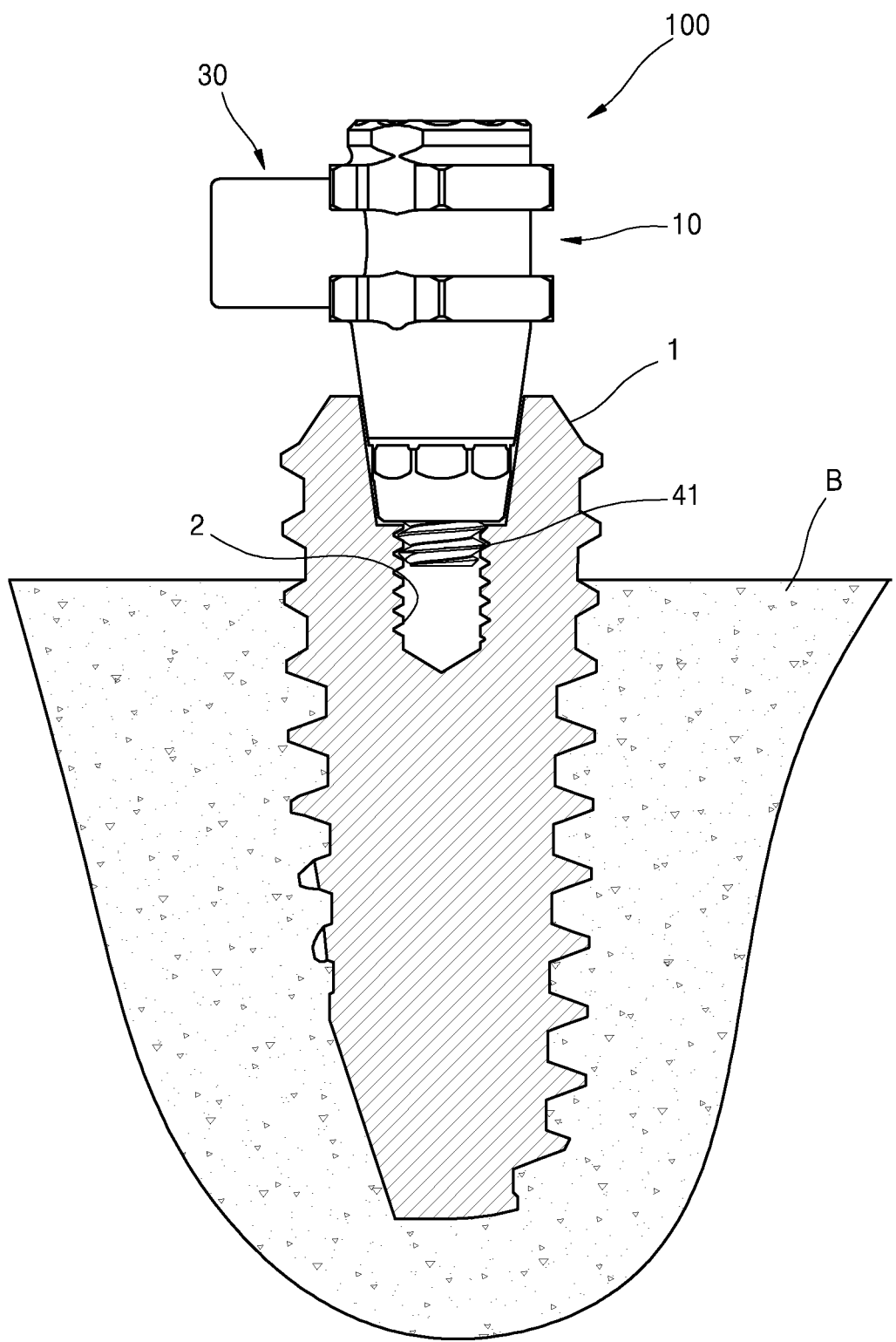
FIG. 10 is a cross-sectional view for explaining a coupled state of an implant abutment to a fixture.

As depicted in FIG. 10, a male screw portion 41 that can be screw coupled to the fixture 1 is formed on a lower end portion of the coupling member 40.

The male screw portion 41 is exposed to the outside through the lower hole 12 of the main body 10.

The coupling member 40 is coupled to the first rotating member 20 so that a relative rotation with respect to each other does not occur when the coupling protrusion 22 and the coupling groove 42 are in a coupled state.

In the current embodiment, since the coupling protrusion 22 of the first rotating member 20 is loosely inserted in the coupling groove 42, the coupling member 40 may have a relative movement in a direction up and down with respect to the first rotating member 20 is possible in a state when the first rotating member 20 is coupled to the coupling member 40.

A second stopper surface 43 that faces downwards by protruding in a radius direction of the first rotational axis C1 is formed along a circumferential direction of the first rotational axis C1 between the male screw portion 41 and the coupling groove 42.

The stopper member 50 confines the position of the separation-prevention groove 33 so that the separation-prevention protrusion 23 of the first rotating member 20 is fixedly positioned without being disengaged from the separation-prevention groove 33 of the second rotating member 30. The stopper member 50 includes a lid 51, a protrusion portion 52, and a accommodation groove 53.

The lid 51 is a disc shape metal member, and is coupled to the upper hole 11 of the main body 10.

An engaging portion 54 that is formed to protrude in a radius direction of the first rotational axis C1 is formed on an outer circumferential surface of the lid 51 along a circumferential direction of the first rotational axis C1.

The engaging portion 54 is a part to be coupled to the engaged portion 111 of the main body 10.

The protrusion portion 52 is a part that protrudes downwards from a lower surface of the lid 51 and is disposed in the internal space 16 of the main body 10.

Figure 4:
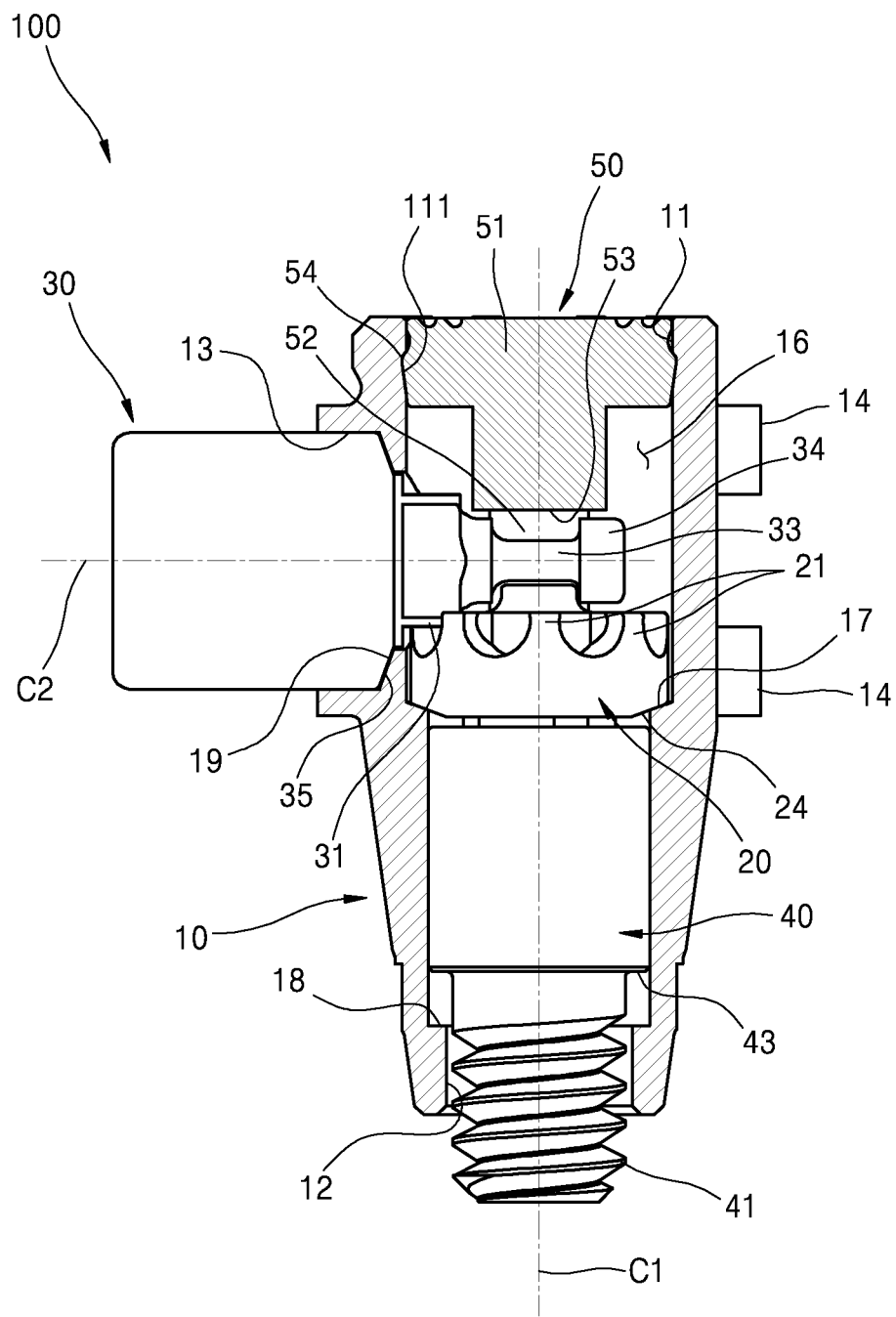
FIG. 4 is a cross-sectional view taken along line III-III of FIG. 1.

The accommodation groove 53 is formed on a lower end of the protrusion portion 52, and confines a position of the second rotating member 30 in upper, left, and right directions by accommodating an end portion of the second rotating member 30. In the current embodiment, as depicted in FIG. 4, the accommodation groove 53 is formed to be able to press an upper end portion of the head portion 34 downwards.

The separation-prevention means prevents the first gear portion 21 of the first rotating member 20 from being disengaged from the second gear portion 31 of the second rotating member 30 while the first rotating member 20 and the second rotating member 30 are rotated. In the current embodiment, the accommodation groove 53 includes the separation-prevention protrusion 23, the separation-prevention groove 33, and the stopper member 50.

An operational principle of the accommodation groove 53 is as follows. In a state that the separation-prevention protrusion 23 of the first rotating member 20 is inserted into the separation-prevention groove 33 of the second rotating member 30, the accommodation groove 53 of the stopper member 50 restricts the head portion 34 of the second rotating member 30 from moving positions in an upward direction and lateral directions and the separation-prevention protrusion 23 restricts the separation-prevention groove 33 from moving position in a lower direction, and thus, the position of the separation-prevention groove 33 of the second rotating member 30 is fixed without being disengaged from the separation-prevention protrusion 23 of the first rotating member 20.

Accordingly, due to the separation-prevention means, the second gear portion 31 may maintain a coupled state with the first gear portion 21, and the second rotating member 30 may maintain a coupled state without being disengaged from the side hole 13 of the main body 10.

Hereinafter, as an example, a method of assembling the implant abutment 100 described above will be described.

First, when the coupling member 40 is inserted through the upper hole 11 of the main body 10, the second stopper surface 43 of the coupling member 40 is engaged with the second stopper 18 of the main body 10, and thus, the coupling member 40 cannot move further downwards.

Next, when the first rotating member 20 is inserted through the upper hole 11, the first stopper surface 24 of the first rotating member 20 is engaged with the first stopper 17 of the main body 10, and thus, the first rotating member 20 cannot move further downwards. At this point, the coupling protrusion 22 of the first rotating member 20 is loosely coupled to the coupling groove 42 of the coupling member 40.

In this way, when the second rotating member 30 is inserted into the side hole 13 of the main body 10 after coupling the first rotating member 20 and the coupling member 40, a third stopper surface 35 of the second rotating member 30 is engaged with the third stopper surface 19 of the main body 10, and thus, the second rotating member 30 is not further moved to the right position. At this point, the separation-prevention groove 33 is inserted into the separation-prevention protrusion 23 of the first rotating member 20.

Finally, when the stopper member 50 is inserted into the upper hole 11 of the main body 10, the engaging portion 54 of the lid 51 is engaged with the engaged portion 111 of the upper hole 11, and thus, the assembly of the implant abutment 100 is completed. At this point, since the accommodation groove 53 restricts the head portion 34 of the second rotating member 30 from moving in an upper direction and lateral directions, the second rotating member 30 is fixedly positioned without being disengaged from the first rotating member 20.

After the assembly is completed, as depicted in FIG. 1, when the second rotating member 30 is rotated in a direction with respect to the second rotational axis C2 by using a tool, such as a small wrench or a hex screwdriver, the first rotating member 20 that is geared with the second rotating member 30 also rotates in the same direction as above and the coupling member 40 that is coupled to the first rotating member 20 is rotated in the same direction with respect to the first rotational axis C1. Here, when the rotational direction of the second rotating member 30 is changed, the rotational direction of the coupling member 40 is also changed.

Accordingly, as depicted in FIG. 10, in the implant abutment 100, the male screw portion 41 of the coupling member 40 may be screw coupled to a screw hole 2 vertically formed on an upper end of the fixture 1 that is implanted in the alveolar bone B or the male screw portion 41 may be disengaged from the screw hole 2 of the fixture 1 by controlling the rotational direction of the second rotating member 30.

The implant abutment 100 having a configuration described above is coupled to the main body 10 to be able to rotate with respect to the first rotational axis C1. Also, the implant abutment 100 includes, on an end portion thereof, a the first rotating member 20 in which the first gear portions 21 are arranged in a circular shape with respect to the first rotational axis C1, and, on the other end portion thereof, the second rotating member 30 that is coupled to the main body 10 to be able to rotate with respect to the second rotational axis C2 which crosses the first rotational axis C1, and has the second gear portion 31 that is coupled to the first gear portion 21 to form a bevel gear structure. Therefore, unlike a conventional implant abutment, a coupling tool, such as a hex driver may be disposed in a horizontal direction that crosses the implanting direction of the fixture 1. Thus, a working space for coupling the fixture 1 in a mouth of a patient may be readily ensured. Accordingly, an assembling work to couple to the fixture 1 may be rapidly completed, and the patient does not need to open mouth for a long hour.

Also, in the implant abutment 100, the coupling tool can be disposed in a horizontal direction that is a direction crossing the implanting direction of the fixture 1, and thus, it is unnecessary for the patient to largely open mouth to ensure a coupling space, and thus, the physical discomfort of the patient is reduced.

Also, since the implant abutment 100 includes a separation-prevention means that prevents the first gear portion 21 of the first rotating member 20 from being disengaged from the second gear portion 31 of the second rotating member 30, while the first rotating member 20 and the second rotating member 30 rotate, the coupled state of the second gear portion 31 with the first gear portion 21 can be maintained, and the coupled state of the second rotating member 30 with the side hole 13 of the portion main body 10 can be maintained without being disengaged from each other.

Also, in the implant abutment 100, the separation-prevention means includes the separation-prevention protrusion 23 formed to protrude on an end portion of the first rotating member 20 and the separation-prevention groove 33 that is formed on an end portion of the second rotating member 30 and can accommodate the separation-prevention protrusion 23 in a state that the first rotating member 20 and the second rotating member 30 are rotated. Therefore, the separation-prevention means can be readily assembled and disassembled.

Also, in the implant abutment 100, the separation-prevention protrusion 23 has a cylindrical shape with the first rotational axis C1 as a center and protrudes upwards along the first rotational axis C1, and the separation-prevention groove 33 is concavely sunk along a circumferential direction of the second rotational axis C2. Therefore, the separation-prevention groove 33 may be readily inserted into the separation-prevention protrusion 23 while inserting the second rotating member 30 into the side hole 13 of the main body 10.

Also, in the implant abutment 100, since the separation-prevention means includes the stopper member 50 that is coupled to the main body 10 and restricts the position movement of the separation-prevention groove 33, the separation-prevention groove 33 may be fixedly positioned without being disengaged from the separation-prevention protrusion 23.

Also, in the implant abutment 100, since the stopper member 50 includes the lid 51 that is coupled to the upper hole 11 of the main body 10, the protrusion portion 52 that protrudes from a lower surface of the lid 51, and the accommodation groove 53 that is formed on an end portion of the protrusion portion 52 and confines a position of the second rotating member 30 by accommodating an end portion of the second rotating member 30, the stopper member 50 realizes a simple structure in which the separation-prevention groove 33 formed on an end portion of the second rotating member 30 may be fixedly positioned without being disengaged from the separation-prevention protrusion 23.

Also, in the implant abutment 100, the main body 10 includes the internal space 16 that can accommodates an end portion of the first rotating member 20 and an end portion of the second rotating member 30 and the upper hole 11 that is formed on an upper end of the main body 10 and is formed to insert the first rotating member 20 into the internal space 16. The lid 51 is mounted in the upper hole 11. Therefore, the first rotating member 20 may be inserted into the internal space 16 of the main body 10 through the upper hole 11, and the upper hole 11 may be closed by using the lid 51 of the stopper member 50.

Also, in the implant abutment 100, the engaging portion 54 is formed on an outer circumferential surface of the lid 51, and the engaged portion 111 that is engaged with the engaging portion 54 is formed on an inner circumferential surface of the upper hole 11. Therefore, a convenient coupling structure, such as a so-called snap fit structure may be easily realized.

Also, the implant abutment 100 includes the coupling member 40 having the male screw portion 41, an end portion thereof is coupled to the other end portion of the first rotating member 20 and the other end portion thereof can be screw coupled to the fixture 1. Therefore, after manufacturing various types of coupling members 40 having the male screw portion 41 having various shapes, a coupling member 40 corresponding to a screw hole 2 of the fixture 1 having a specific shape may be selected and used.

Also, in the implant abutment 100, the coupling protrusion 22 having a protrusion shape is formed on the other end portion of the first rotating member 20, and the coupling groove 42 that is formed on an end portion of the coupling member 40 and is coupled to the coupling protrusion 22 so as not to have a relative rotation with respect to the first rotational axis C1. Therefore, the first rotating member 20 and the coupling member 40 may be simply coupled to each other.

Also, in the implant abutment 100, the coupling member 40 may have a relative movement with respect to the first rotating member 20 in a vertical direction which is the direction of the first rotational axis C1 in a state when the separation-prevention groove 33 is coupled to the coupling protrusion 22. Therefore, in the process of coupling the male screw portion 41 to the screw hole 2 of the fixture, the coupling member 40 does not pull the first rotating member 20 downwards, and thus, there is no adverse effect to the coupling state of the first gear portion 21 and the second gear portion 31.

Also, in the implant abutment 100, the main body 10 includes the internal space 16 that can accommodate the first rotating member 20 and the second rotating member 30; the upper hole 11 that is a hole formed on an upper end portion of the main body 10 so that the first rotating member 20 is inserted into the internal space 16; the lower hole 12 that is a hole formed on a lower end portion of the main body 10 so that the male screw portion 41 is exposed to the outside; and the side hole 13 that is a hole formed on a side of the main body 10 so that the second rotating member 30 is inserted into the internal space 16. Therefore, the first rotating member 20 and the second rotating member 30 may be readily assembled to the main body 10.

Also, in the implant abutment 100, the main body 10 includes the projection portion 14 that protrudes in a radius direction of the first rotational axis C1 from the outer circumferential surface of the main body 10. Thus, when compared to a case when the projection portion 14 is not included in the main body 10, combination to an impression material or an adhesive is easy.

In the current embodiment, the male screw portion 41 is provided on the other end portion of the coupling member 40 which is an additional member. However, the male screw portion 41 may be formed on the other end portion of the first rotating member 20 without using the coupling member 40.

In the current embodiment, the separation-prevention means includes the separation-prevention protrusion 23 formed on the first rotating member 20 and the separation-prevention groove 33 formed on the second rotating member 30. However, on the contrary, the separation-prevention protrusion 23 may be formed on the second rotating member 30 and the separation-prevention groove 33 may be formed on the first rotating member 20.

While the inventive concept has been particularly shown and described with reference to exemplary embodiments thereof, it will be understood that various changes in form and details may be made therein without departing from the spirit and scope of the following claims.

What is claimed is:

1. A dental implant abutment that is coupled to a fixture that becomes an artificial tooth root by being implanted to an alveolar bone, the implant abutment comprising:
   a main body having an internal space and an upper hole, a lower hole and a side hole;
   a first rotating member located in the internal space of the main body which is able to rotate within the main body with respect to a first rotational axis, and which has a first gear portion and a separation-prevention protrusion on an upper end portion thereof, and is operably connected with a lower male screw portion sized to extend downwardly through the body lower hole and screw coupled to the fixture;
   a second rotating member located in the body side hole and internal space of the main body which is able to rotate with respect to a second rotational axis which crosses the first rotational axis, and which has a second gear portion that engages the first gear portion of the first rotating member whereby rotation of the second rotating member causes rotation of the first rotating member, and a separation-prevention groove which receives the separation-prevention protrusion of the first rotating member; and
   a stopper member that is coupled to the main body and limits movement of the second rotating member so that the separation-prevention protrusion is within the separation-prevention groove.

2. The dental implant abutment of claim 1, wherein the separation-prevention protrusion of the first rotating member has a cylindrical shape with the first rotational axis as a center and upwardly protrudes along the first rotational axis, and the separation-prevention groove of the second rotating member is concavely formed around a circumference of a portion of the second rotating member.

3. The dental implant abutment of claim 1, wherein the stopper member comprises:
   a lid;
   a protrusion portion that protrudes from a lower surface of the lid; and
   an accommodation groove that is formed in an end portion of the protrusion portion and receives an end portion of the second rotating member to limit movement of the second rotating member.

4. The dental implant abutment of claim 3, wherein the lid is mounted in the upper hole of the main body.

5. The dental implant abutment of claim 4, further comprising:
   an engaging portion is formed on an outer circumferential surface of the lid, and
   an engaged portion formed on an inner circumferential surface of the upper hole;
   wherein the engaging portion of the lid engages by snap fitting into the engaged portion of the main body.

6. The dental implant abutment of claim 1, further comprising a coupling member having an upper end which is coupled to a lower end portion of the first rotating member, and a lower end having the lower male screw portion that is screw-coupled to the fixture.

7. The dental implant abutment of claim 6, wherein
   the lower end portion of the first rotating member has a coupling protrusion having a protrusion shape; and
   the coupling member has a coupling groove shaped to receive the protrusion shape of the coupling protrusion;
   whereby the first rotating member and coupling member are engaged and rotate together and are prevented from relative rotation with respect to each other.

8. The dental implant abutment of claim 1, wherein the main body comprises a projection portion that extends outwardly from an outer circumferential surface of the main body.

* * * * *